United States Patent [19]

Knepshield et al.

[11] 4,177,814

[45] Dec. 11, 1979

[54] SELF-SEALING CANNULA

[75] Inventors: William R. Knepshield, Malvern; Jerry Polizzi, Morrisville; Allen H. Okamoto, Ambler, all of Pa.

[73] Assignee: KLI, Incorporated, Newtown, Pa.

[21] Appl. No.: 870,478

[22] Filed: Jan. 18, 1978

[51] Int. Cl.² ............................................. A61M 25/00
[52] U.S. Cl. .................................. 128/348; 128/347; 128/221
[58] Field of Search ................... 128/348, 347, 214.4, 128/2 A, 2 F, 221, 272, DIG. 16, 6

[56] References Cited

U.S. PATENT DOCUMENTS

| | | | |
|---|---|---|---|
| 3,097,646 | 7/1963 | Scislowics | 128/214.4 |
| 3,313,299 | 4/1967 | Spademan | 128/347 X |
| 3,454,006 | 7/1969 | Langdon | 128/214.4 |
| 3,853,127 | 12/1974 | Spademan | 128/214.4 |
| 3,994,287 | 11/1976 | Turp et al. | 128/347 |
| 4,000,739 | 1/1977 | Stevens | 128/214.4 |
| 4,079,738 | 3/1978 | Dunn et al. | 128/214.4 |

*Primary Examiner*—Stephen C. Pellegrino
*Attorney, Agent, or Firm*—Miller & Prestia

[57] ABSTRACT

Self sealing cannula automatically maintains insufflation pressure in a body cavity. A slotted elastomeric valve is positioned in the valve seat with the slot disposed over the passage. The elastomeric valve is compressed to seal the slot, thus sealing the cannula passage.

A surgical instrument such as a trocar or laparoscope may be slid through the cannula passage, which remains sealed regardless of the presence or absence of the surgical instrument within the passage.

12 Claims, 8 Drawing Figures

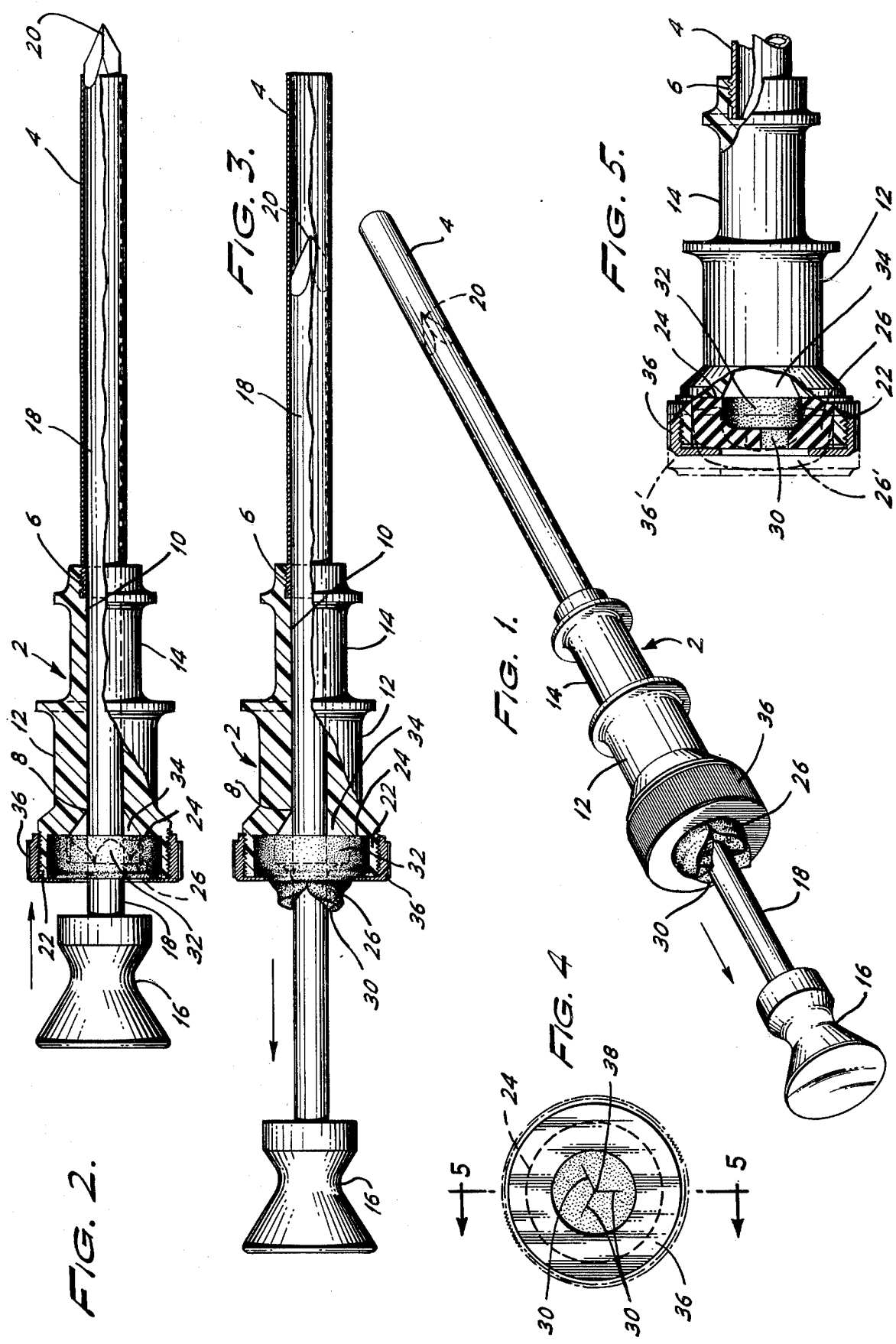

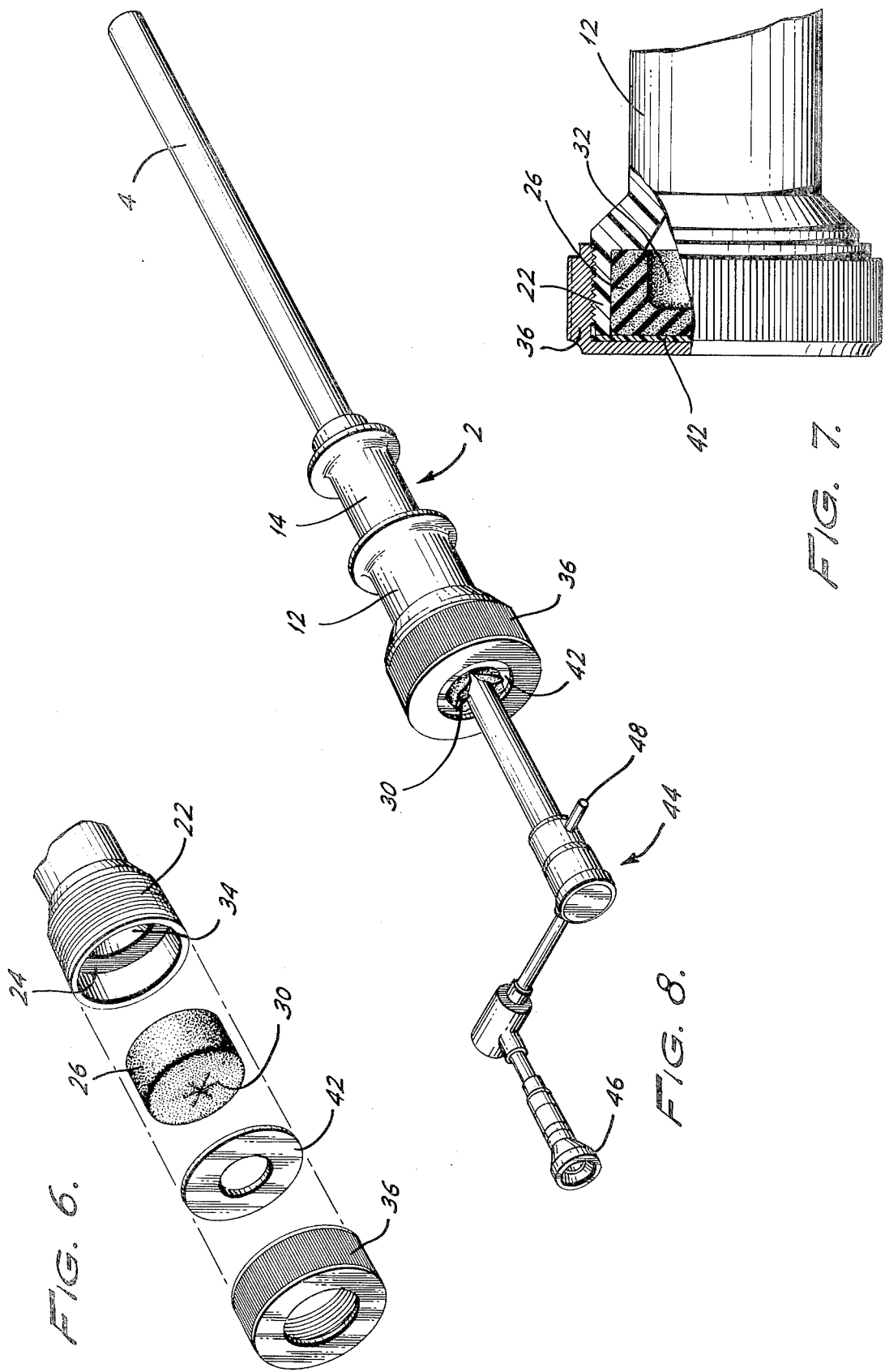

SELF-SEALING CANNULA

BACKGROUND OF THE INVENTION

1. Field of the Invention

This application relates to a self sealing cannula adapted for use in conjunction with insufflatory surgical techniques wherein a body cavity is filled with pressurized gas to maintain the cavity under a certain predetermined pressure. When the presently disclosed cannula is utilized, the proper pressure is automatically maintained within the cavity without requiring the surgeon to manually adjust or regulate any valve whatsoever.

2. Background of the Invention

Numerous surgical instruments have included sealing means to prevent the flow of fluids to or from the patient's body. For instance, U.S. Pat. No. 3,970,089 discloses a seal device for a catheter comprising an elastomeric member having a lumen through which the catheter is passed. By distending the elastomeric member to constrict the lumen, a seal against egress of blood along the interface between the catheter and the innermost surface of the member is effected.

However, of primary interest to the present invention are those cannula assemblies that are designed to maintain gas pressure within the body. Such an apparatus is disclosed in U.S. Pat. No. 3,994,287 (Turp, et al). Gas pressure within the body cavity is maintained by the use of a flexible ring with an aperture therein that is positioned within an annular valve seat portion of the cannula. A collar is placed over the flexible ring to seal the valve seat sidewalls. However, sealing is realized only when a portion of a surgical instrument is disposed within the cannula passage. Accordingly, when the surgeon removes the instrument from the passage, the seal is lost, and other means must be employed to maintain suitable gas pressure within the body cavity.

U.S. Pat. No. 3,989,049 (Yoon) discloses, inter alia, another cannula (FIG. 6) provided with a trumpet valve to maintain the desired pressure within the anatomical cavity. However, the trumpet valve must be manually regulated with a rather cumbersome procedure. The surgeon must adjust the valve, remove the trocar from the cannula, and replace it with another instrument, for instance, a laparoscope or elastic ring applicator.

Accordingly, it is an object of the present invention to provide a cannula which is self-sealing and is ideally adapted for use in insufflatory surgical procedures.

Further, it is a more specific object to provide a cannula having positive sealing even after the surgical instrument has been removed from the cannula passage.

It is an even more specific object to provide a cannula that automatically seals without requiring manipulation of any valve, so that the surgeon's hands may remain free for other purposes.

Other objects and advantages of this invention will appear in further detail hereinafter.

SUMMARY OF THE INVENTION

These and other objects are met by the self sealing cannula disclosed herein. It has now been discovered that surprisingly effective sealing can be obtained by incorporating a slotted elastomeric valve into the cannula itself. In a preferred form, the elastomeric valve is positioned in a valve seat disposed within a flanged section of the cannula body. The slot is disposed over the cannula passage. A compression means, such as a knurled sealing nut, engages the flanged body section and compresses the elastomeric valve inwardly in the plane thereof to seal the slot even after an instrument such as a trocar or a ring applicator has been withdrawn from the cannula.

No manipulative effort at all is required to actuate the seal since the compression means automatically performs this function and the seal is effected even in the absence of any instrument within the cannula passage.

The foregoing will become apparent from the following detailed description of a preferred embodiment, with reference to the accompanying drawings.

BRIEF DESCRIPTION OF THE DRAWINGS

In the drawings:

FIG. 1 is a perspective view of a self sealing cannula in accordance with the invention in combination with a trocar, a portion of which is slidably disposed within the cannula passage;

FIG. 2 is a side elevation of the apparatus shown in FIG. 1, shown with the associated trocar in its extended position, certain parts being broken away, in order better to illustrate certain features of the invention;

FIG. 3 is another side elevation similar to FIG. 2, with the associated trocar in its retracted position, certain parts also being broken away;

FIG. 4 is a fragmentary view of the head end of the cannula body portion showing one form of elastomeric valve, valve seat and sealing nut, the valve seat being outlined by use of a dot-dash circle;

FIG. 5 is a cutaway detailed sectional view taken along the lines and arrows 5—5 which appear in FIG. 4;

FIG. 6 is a partial exploded perspective view of another embodiment of the invention;

FIG. 7 is a cutaway side view of the apparatus shown in FIG. 6; and

FIG. 8 is a perspective view of the self sealing cannula shown in FIG. 6, in combination with a laparoscope, a portion of which is slidably disposed within the cannula passage.

DETAILED DESCRIPTION OF PREFERRED EMBODIMENTS

In describing the specific form of the invention selected for illustration in the drawings, specific terms have been utilized. These specific terms are used to teach the invention in a manner that will be readily understood by those skilled in the art, and they do not limit the scope of the invention in a manner that will be readily understood by those skilled in the art, and they do not limit the scope of the invention as defined in the claims.

With reference to the drawings and especially to FIGS. 1 through 3 thereof, there is shown a self sealing cannula in accordance with the invention. The cannula comprises body 2 and elongated sleeve 4. Sleeve 4 is connected to body 2 via threads 6 (FIGS. 2 and 3). Of course, other suitable means for connecting the sleeve and body may be employed. Epoxy resin may be provided around threads 6 to seal the body and sleeve.

Body 2 includes bore 8 that extends longitudinally through the body. The sleeve and body bore 8 communicate to define a cannula passage 10 that extends longitudinally through the instrument. The body is advantageously composed of acetal, polysulfone, any high temperature thermoplastic, or stainless steel. However, any material is acceptable as long as it may be sterilized by gas, autoclave, or cold sterilization and the like.

The body 2 includes concavely rounded finger grip portions 12, 14 that are provided adjacent each other along the exterior of body 2 to facilitate easy grasping and manipulation by the surgeon.

A trocar, comprising handle 16 at the rearward end of shaft 18 is shown slidably disposed within the cannula passage 10. The forward end portion of shaft 18 is sharpened to a point as shown at 20. The cannula may be utilized with other types of pointed or blunted trocars. The trocar illustrated in the drawings has a triangular point, but other point configurations may also be used.

The body 2 includes flanged section 22 disposed at its rearward end, having an interior portion forming a valve seat 24 that is coaxially disposed around cannula passage 10. An elastomeric valve 26 is positioned within the seat 24. The valve 26 includes a slotted portion 30 that is positioned over the cannula passage.

As shown, the valve 26 has the shape of an annular disc that is indented in an annular region thereof to form a cup shape as shown at 32 in FIGS. 2 and 3. The indented region itself is coaxially positioned over the cannula passageway, and slotted portion 30 is located in the indentation.

The valve flaps in the drawings are shown in somewhat exaggerated positions in FIGS. 2 and 3 to effectively illustrate their posture as the trocar is slidably moved in relation to the cannula.

As seen in FIGS. 2 and 3, body 2 includes a counter bore section 34 of converging diameter located adjacent valve seat 24. The smallest diameter portion of counter bore 34 mates with cannula body bore 8; the widest portion of the counter bore 34 is positioned next to the valve seat 24.

A knurled sealing nut 36 is threaded to body 2 and serves as a means for compressing valve 26 within the seat 24 so as to seal the slotted portion 30 of the valve. Even when trocar shaft 18 is not disposed in passage 10 through slot 30, the slot is sealed due to this compressive force.

The valve 26 is comprised of a bio-compatible elastomer, preferably silicone elastomer, but other elastomeric materials such as rubber will suffice.

As shown in FIG. 2, when the trocar is pushed forwardly within the cannula, sharp edge 20 of the trocar extends from the forward end portion of sleeve 4. The counter bore area 34 accommodates momentary forward displacement of slotted region 30.

In FIG. 3 it is apparent that rearward withdrawal of the trocar causes portions of the valve 26 around the slots 30 to be pulled rearwardly along trocar shaft 18. However, the entire assembly remains sealed during both forward and rearward sliding of the shaft 18 within the cannula passage 10 due to compressive action of sealing nut 36 upon the valve 26.

FIG. 4 shows the preferred arrangement of the valve slots. Here, three slots are cut in the valve that intersect with each other at central point 38. The three slots each extend from point 38 at approximately 120° intervals. Other numbers of slots may be used. (FIG. 6).

It is apparent to those skilled in the art that varied valve structures can be employed in accordance with the inventive concepts herein disclosed. Indeed, various dimensional changes, such as valve thickness, may be made to the valve illustrated in the drawings. Further, varied valve slot configurations may be employed such as 5, 6, or 8 pronged slots.

FIG. 5 illustrates a preferred form of the valve and valve seat combination in detail. The reference numeral 36' shows the nut 36 in phantom, before it is threaded to the flanged section 22. Reference numeral 26' shows the valve 26 in its relaxed condition prior to threading of the nut 36 to flanged section 22. Thus, it can be seen that nut 36 compresses the valve within the valve seat area 24 to seal the slotted region 30 and also to prevent any gas escape along the sidewall of the annular valve seat.

Advantageously, the self sealing cannula is used in conjunction with insufflatory surgical techniques wherein a needle type instrument first punctures the skin in a desired body cavity region. Usually, the needle houses a stylet or the like that introduces a gas, e.g., carbon dioxide, from a pressurized container into the body cavity. After the cavity has been inflated, the sharp point 20 of the trocar—cannula combination as shown in FIGS. 1 through 3 of the drawings is caused by the surgeon to make an incision and thereby enters the cavity. The trocar may then be removed, and an elongated endoscope, such as a laparoscope, can be inserted through the cannula to view the anatomical cavity. Other instruments, such as a ring applicator for tubal ligation, may be inserted.

FIGS. 6–8 show another embodiment of the invention adapted for use with instruments having larger diameter shafts than the trocar depicted in FIGS. 1 through 3. Here, a wiper seal 42 is interposed between the valve 26 and nut 36. The wiper seal 42 may advantageously be composed of silicone, and the outside diameter of the wiper seal 42 is approximately equal to the inside diameter of the nut 36. The primary function of the wiper seal 42 is to insure a tight seal when relatively large diameter instrument shafts are slidably disposed within the passage 10 by restricting the movement of the flaps of valve 26.

FIG. 8 illustrates the cannula shown in FIGS. 6 and 7 in combination with a laparoscope 44 slidably disposed in the cannula passage. As is conventional in the art, the laparoscope includes an eyepiece 46 and a tubular extension 48 which comprises a bundle of fiberoptic strands. The extension 48 is adapted to be connected with a light source as is well known in the art.

The disclosed cannula is advantageously utilized in ligation of fallopian tubes by an elastic ring applicator of the types disclosed and claimed in U.S. patent applications, Ser. Nos. 305,187 (Lampman, et al) filed Aug. 15, 1975, and 725,272 (Polk, et al) filed Sept. 21, 1976, both applications assigned to KLI, Inc., of Ivyland, Pa. These commonly assigned elastic ring applicators may be used by themselves, or combined with laparoscopes. In either case, the elongated instrument is simply slidably positioned within the cannula passage 10, a fallopian tube is then grasped by the applicator, and an elastic ring is then ejected and stretched about the grasped fallopian tube.

It will be apparent that the self sealing cannula disclosed and claimed herein provides many advantages over prior art sealing cannulas. For instance, a seal is maintained even when an instrument is not disposed within the cannula passage. Further, no manipulative effort is needed to actuate the seal.

The disclosed cannula is also easily cleaned, and it can be readily assembled and disassembled.

This invention has been described in relation to certain surgical instruments such as endoscopes (including laparoscopes), trocars and elastic ring applicators that can be operatively combined with the disclosed cannula. Description of the above instruments is for illustrative purposes only, as it is apparent that any tubular, elongated surgical instrument may be slidably disposed within the cannula passage 10.

Further, although this invention has been disclosed with reference to certain specific forms thereof, it will be appreciated that a wide variety of modifications may be made without departing from the spirit and scope of this invention. For example, equivalent parts and elements may be substituted for those specifically shown and described, certain features may be used independently of the use of other features, and parts may in some cases be reversed, all without departing from the spirit and scope of the invention as defined in the appended claims.

The following is claimed:

1. A self sealing cannula for insufflatory surgical procedures wherein an operative body cavity is maintained under gas pressure during said surgical procedure, said cannula comprising an elongated sleeve having a cannula passage constructed for receiving surgical instruments therethrough and for penetrating into said operative body cavity to facilitate insertion and withdrawal of a surgical instrument while retaining said cannula in situ and while retaining gas pressure in said body cavity notwithstanding withdrawal of said surgical instrument, said cannula having a valve seat coaxially disposed about the cannula passage through which said surgical instrument is adapted to extend, an elastomeric valve positioned against the valve seat in a position to block said passage, said elastomeric valve having a slotted portion positioned along said cannula passage in a position to be penetrated by said surgical instrument upon insertion thereof, and having sufficient elasticity to yield to permit such insertion, and compression means carried by said cannula and positioned to apply inwardly directed pressure to said elastomeric valve to compress the elastomeric valve inwardly toward said slotted portion thereof for sealing the cannula passage against outward flow of said pressurized gas therethrough after withdrawal of said surgical instrument from said cannula passage.

2. A self sealing cannula as recited in claim 1 wherein the compression means comprises a sealing nut.

3. A self sealing cannula as recited in claim 1 further including a wiper seal interposed between the elastomeric valve and the compression means.

4. A self sealing cannula as recited in claim 1 wherein the cannula includes a body having a counter bore section located adjacent the valve seat and comprising a counter bore of converging diameter, the body bore mating with the counter bore along the smallest diameter portion of the counter bore.

5. A self sealing cannula as recited as recited in claim 1 wherein the elastomeric valve includes an annular disc having an annular indentation, the indentation being coaxially disposed over the passage.

6. A self sealing cannula as recited in claim 1 wherein the valve comprises silicone.

7. A self sealing cannula as recited in claim 1 wherein the elastomeric valve includes three slots, the slots intersecting at a point that is coaxial with respect to the passage.

8. A self sealing cannula as recited in claim 7 wherein the slots extend from the point at approximately 120° intervals.

9. The self-sealing cannula defined in claim 1, wherein said elastomeric valve is cup shaped.

10. The self-sealing cannula defined in claim 1, wherein said elastomeric valve has an indented portion substantially aligned with said passageway.

11. The self-sealing cannula defined in claim 10, wherein said slotted portion is located in said indented portion.

12. The self-sealing cannula defined in claim 10, wherein said elastomeric valve includes an axially elongated portion surrounding said indented portion, and wherein said compression means includes a portion located adjacent to said elongated surrounding portion of said elastomeric valve, with capacity to exert a substantially axial force upon said surrounding portion and to translate said force to create a lateral compression of the indented portion of said elastomeric valve in order laterally to squeeze said slotted portion thereof.

* * * * *